United States Patent [19]

Stansfeld

[11] Patent Number: 4,466,272
[45] Date of Patent: Aug. 21, 1984

[54] FLUID DENSITY TRANSDUCER

[75] Inventor: James W. Stansfeld, Alton, England

[73] Assignee: The Solartron Electronic Group Limited, Farnborough, England

[21] Appl. No.: 382,905

[22] Filed: May 28, 1982

Related U.S. Application Data

[63] Continuation of Ser. No. 203,841, Nov. 4, 1980, Pat. No. 4,354,377.

[30] Foreign Application Priority Data

Nov. 6, 1979 [GB] United Kingdom ................ 7938367

[51] Int. Cl.$^3$ .............................................. G01N 9/00
[52] U.S. Cl. ...................................................... 73/32 A
[58] Field of Search ............................... 73/32 R, 32 A

[56] References Cited

U.S. PATENT DOCUMENTS 3,298,221  1/1967  Miller et al. ........................ 73/32 A
3,585,843  6/1971  Stansfeld ............................ 73/32 A
4,007,627  2/1977  Stansfeld ............................ 73/32 A Primary Examiner—James J. Gill
Attorney, Agent, or Firm—Dale Gaudier

[57] ABSTRACT

A fluid density transducer with a vibrating tube 16 coupled to excitation pick-up transducers 32 utilizes an elliptical tube 16, having a small degree of ellipticity, to compensate for the variation in the natural frequency of vibration, resulting from a variation in the fluid pressure, i.e. a rise in fluid pressure tending to lower the frequency produces a more circular and hence stiffer tube cross-section tending to increase the frequency. A sealed evacuated chamber 36, formed by connecting together cylindrical nodal masses 24 and 26 using a flexible coupling 28, is used to enclose the vibrating tube 16, thus avoiding the risk of contaminating, and thereby also affecting the calibration of, the tube 16. The tube is supported at each end by a spring plate 12 fixed around its outer periphery to a collar 10 and around its inner periphery to an end-plate 25 of the nodal mass 24 or 26. This provides rigid transverse support and allows use of the transducer in any orientation while accommodating small axial movements of the tube at either end.

3 Claims, 5 Drawing Figures

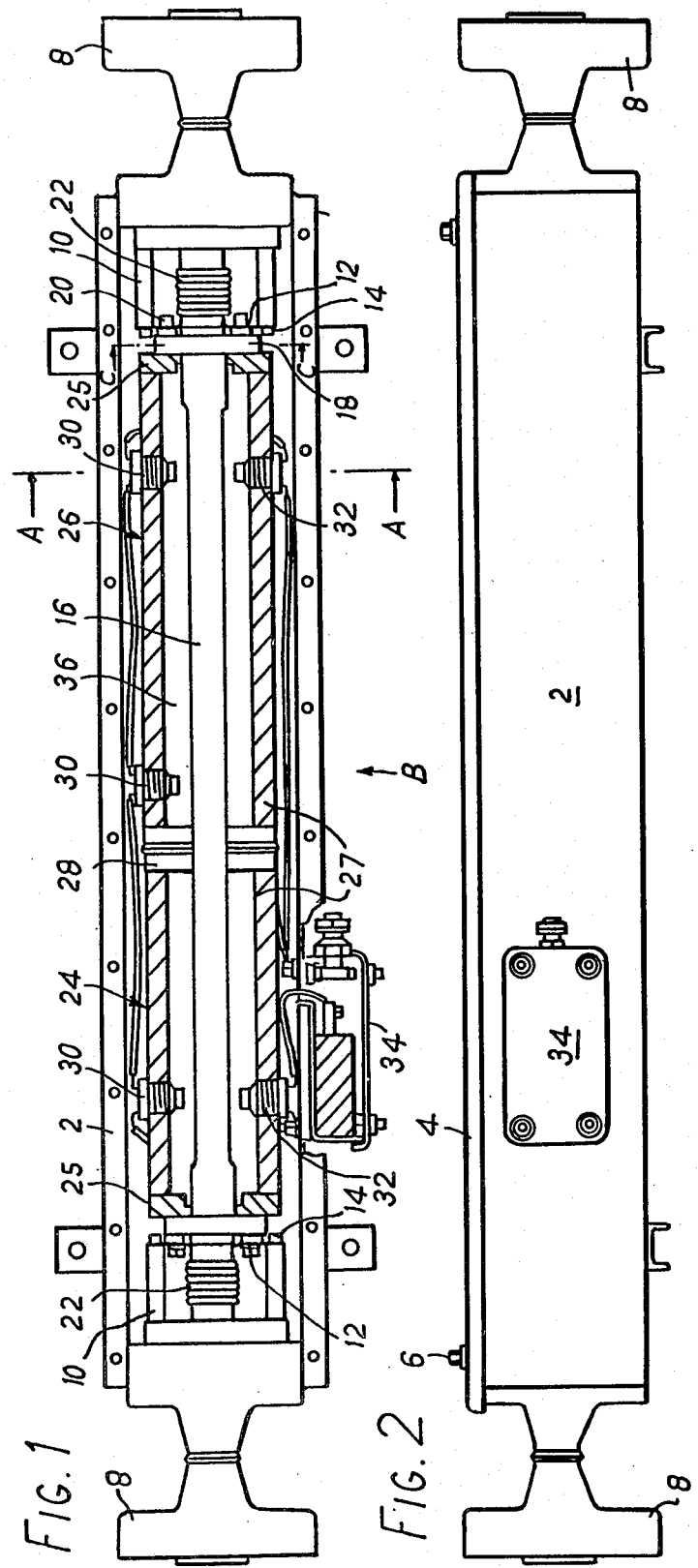

FLUID DENSITY TRANSDUCER

This is a continuation of application Ser. No. 203,841, filed Nov. 4, 1980, now U.S. Pat. No. 4,354,377.

The present invention relates to a fluid density transducer of the type in which natural transverse vibrations are excited in a tube containing the fluid; the frequency of the vibration is affected by the density of the fluid which affects the mass per unit length of the fluid-filled tube. Transducers of this type have been known for many years and examples are described in our British Patent Specification Nos. 1,158,790 and 1,280,997.

Both these specifications are to some extent concerned with the problem that the frequency of vibration of the tube is also influenced by the pressure of the fluid. Specification No. 1,280,997 suggests compensating for this by using rubber inserts at the ends of the tube; with many fluids the presence of such inserts, as possible sources of contamination, is undesirable.

Specification No. 1,158,790 describes a twin-tube transducer in which increase in pressure tends both to expand and elongate the tubes, producing counterbalancing effects so far as the frequency of vibration is concerned. Twin-tube transducers are more complex and expensive than single-tube transducers and are not so easy to install in-line.

The object of the present invention is to provide a simple transducer in which the tube is a single tube of approximately circular cross-section, whereby the pressure-dependent effect which has to be compensated for is the increase in circumferential stress caused by a rise in fluid pressure, which stress is equivalent in its effect to longitudinal compression of the tube. Such compression decreases the transverse rigidity of the tube, thereby lowering the natural frequency.

It is known that the frequency of vibration of a tube of elliptical cross-section is dependent on the fluid pressure inside the tube. An increase in pressure reduces the ellipticity, stiffens the tube and increase the frequency of vibration. British Specification No. 1,088,940 discloses a *pressure* transducer which uses this effect, employing highly elliptical tubes. The aforementioned specification No. 1,158,790 also suggests (see FIG. 7 of the specification) the use of highly elliptical tubes in a twin-tube transducer as a means of confining vibrations to the desired plane. Such a transducer would clearly only be usable when the fluid was kept at a standard pressure; otherwise the variation of frequency with pressure would swamp variations with density.

The present invention provides a fluid density transducer comprising a tube extending between two node-determining devices, and an electrical transducer arrangement coupled to the tube for exciting natural transverse vibrations and providing an oscillatory electrical signal representative of the frequency of vibration, wherein the tube has a small degree of ellipticity with the minor axis of the ellipse parallel to the direction of the vibration, the ellipticity being so small that the principle parameter of a fluid in the tube affecting the frequency of vibration is the density of the fluid, but being sufficient for the increase in frequency arising from stiffening of the tube when the pressure of the fluid rises to compensate for the decrease in frequency arising from increased circumferential stress when the pressure of the fluid rises.

The invention is also concerned with the problem of enclosing the tube in a sealed, evacuated enclosure. The aforementioned specification No. 1,280,997 mentions that this may be desirable to prevent condensation of liquid on the tube. It is more generally desirable to protect the tube from all forms of contamination, particularly when an external housing is opened up for maintenance of electrical transducers.

According to the present invention there is also provided a fluid density transducer comprising a tube extending between node-determining masses, and an electrical transducer arrangement coupled to the tube for exciting natural transverse vibrations and providing an electrical signal representative of the frequency of vibration, wherein the tube is protected from contamination by a sealed, evacuated container formed by connecting together the node determining masses.

The invention is further concerned with the problem of supporting the tube in such a way that the transducer can be installed in any orientation while nevertheless allowing axial movement of the ends of the tube, e.g. to accommodate thermal expansion.

According to the invention there is still further provided a fluid density transducer comprising a tube extending between node-determining masses, and an electrical transducer arrangement coupled to the tube for exciting natual transverse vibrations and providing an electrical signal representative of the frequency of vibration, wherein the tube is supported at each end relative to a supporting structure by a resilient annular plate connected around one periphery to the supporting structure and around the other periphery of the tube.

The tube is preferably vibrated at a harmonic other than the fundamental frequency, e.g. the third harmonic, as we have found that this is the best way of increasing accuracy and repeatability of results in a single tube transducer.

This invention will be described in more detail, by way of example, with reference to the accompanying drawings, in which:

FIG. 1 is a plan view, partially in section, of an embodiment of the invention, with a cover plate removed;

FIG. 2 is a side elevation of the embodiment of FIG. 1;

Figure 3:
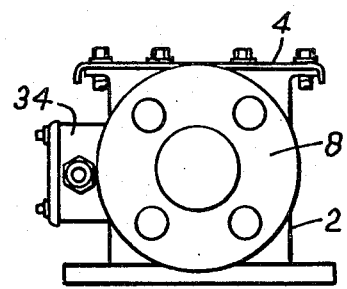
FIG. 3 is an end elevation of the embodiment of FIG. 1.

Referring to FIGS. 1, 2 and 3, an external housing 2 of a fluid density meter is normally closed by a cover plate 4 held by screws 6 and includes welded-in flange pieces 8 for connecting the meter in-line. Support collars 10 are fixed to the insides of the flange pieces and centrally-apertured spring plates 12 are fixed across the inner ends of the collars by bolts 14. A vibrating tube 16, formed of Ni-Span-C (Registered Trade Mark) and of substantially circular cross section has two end plates or flanges 25 welded on to it close to its ends. The tube is supported by the spring plates 12 by way of the end plates 25 and bellows flanges 18; bolts 20 pass through the spring plates 12 and flanges 18 into the end plates 25. The ends of the tube are thus rigidly supported transversely and are sufficiently supported axially to allow the meter to be installed in any orientation while allowing axial movement of the ends of the tube, e.g. to accommodate thermal expansion. The ends of the tube do not contact the bellows flanges 18 and in order to provide a complete seal, O-rings (not shown) are fitted between the bellows flanges 18 and the end plates 25.

Figure 5:
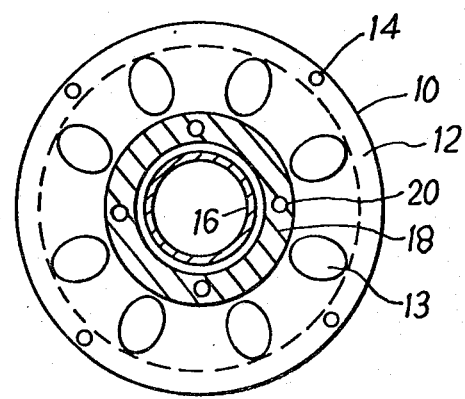
FIG. 5 is a section on line C—C in FIG. 1, to a larger scale than FIGS. 1 to 4.

FIG. 5 shows the vibrating tube 16 passing with substantial clearance through the bellows flange 18 as well as the location of the bolts 14 and 20 which fix the spring plate 12 to the collar 10 and flange 18 respectively In a modified construction the spring plate 12 is welded to the collar 10, which is also welded to the end flange 8, thereby providing a sealed structure which eliminates the need for any O-ring or other such seals. In order to allow this welded construction, the spring plate 12 must be reasonably thick, say as much as 0.4 mm. In order then to reduce the stiffness of the plate a plurality of recesses 13 are provided in its face.

At the end of the tube, a flexible bellows 22 connects the corresponding bellows flange 18 to the corresponding flange piece 8. Coaxially arranged cylindrical end blocks or nodal masses 24 and 26 are rigidly coupled to the vibrating tube 16 at the two ends and are thereby also supported by the spring plates 12. Each block is formed by one of the end plates 25 welded to the tube 16 and a cylindrical sleeve 27. The sleeves 27 extend towards each other from the plates 25 and have spaced proximate ends at an intermediate point along the tube 16. A short flexible coupling 28 having substantially the same diameter as the cylindrical sleeves 27 is used to connect the sleeves 27 so as to form a gas-tight cylindrical chamber 36 about the vibrating tube 16. This chamber is evacuated and sealed in manufacture.

A conventional pick-up and drive coil arrangement operating on a third harmonic excitation principle, as disclosed in British Patent Specification No. 1,280,997 is used to excite natural transverse vibrations of the tube 16. The arrangement includes pick-up coils 30 and drive coils 32 screwed into the nodal masses 24 and 26 at points spaced along the axis of the vibrating tube 16. The pick-up coils 30 are also used to provide a signal representative of the frequency of vibration of the vibrating tube 16. The pick-up coils 30 and drive coils 32 are connected to an output unit 34 secured to the outside of the external housing 2. The particular form of excitation and pick-up arrangement employed forms no part of the present invention.

In operation, the fluid, of which the density is to be measured, is passed through the transducer, entering at one end of the vibrating tube 16 and leaving at the other. The vibrating tube 16 is excited into the third harmonic of the natural transverse vibration by the drive coils 32. The mode is maintained by feedback from the pick-up coils 30 to the drive coils 32, through the output unit 34, which also provides the output signal.

Figure 4:
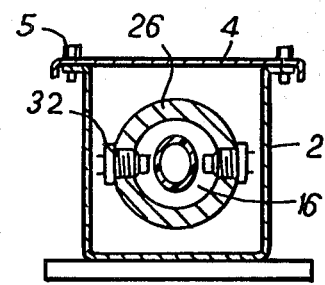
FIG. 4 is a section on the line A—A in FIG. 1.

Compensation for the effects of fluid pressure on the natural frequency of vibration of the tube 16 is achieved by making the vibrating tube 16 slightly elliptical, having a minor axis parallel to the direction of the transverse vibrations. As the fluid pressure increases, the vibrating tube 16 tends to revert to a circular, stiffer cross-section, thus raising the natural frequency. This compensates for the increased circumferential stress, due to the rise in fluid pressure, causing a reduction in the transverse rigidity of the vibrating tube 16 and hence a lowering of the natural frequency of vibration. The degree of ellipticity required to achieve this result is small. For example, a 25 mm diameter tube 16 may be squashed to an ellipse having a minor axis diameter of 23 to 24 mm. The squashing-in of the tube is illustrated in an exaggerated manner in FIG. 1 and the ellipticity is shown in an exaggerated manner in FIG. 4.

During maintenance of the transducer the top cover plate 4 is removed; however the vibrating tube 16 is enclosed in a sealed, evacuated chamber 36. Thus the risk of contaminating, and thereby also affecting the calibration of the vibrating tube 16 is avoided. Furthermore the chamber 36 is formed by elongating, and joining with the flexible coupling 28, the nodal masses 24 and 26, thus increasing their dynamic mass and efficacy as end blocks. The coupling 28 is flexible enough not to couple the nodal masses 24 and 26 dynamically.

I claim:

1. A fluid density transducer comprising a tube extending between node-determining masses, and an electrical transducer arrangement coupled to the tube for exciting natural transverse vibrations and providing an electrical signal representative of the frequency of vibration, wherein the tube is supported at each end relative to a supporting structure by a resilient annular plate connected around one periphery to the supporting structure and around the other periphery to the tube, and said tube is provided with a flexible connection for passage of fluid at each end thereof.

2. A fluid density transducer according to claim 1, wherein the outer periphery of the plate is attached to a collar integral with the supporting structure, and the inner periphery of the plate is attached to a part of the corresponding node-determining mass.

3. A fluid density transducer according to claim 1, wherein the natural transverse vibrations are at a harmonic higher than the fundamental frequency.

* * * * *